United States Patent [19]

Shogen et al.

[11] Patent Number: 4,882,421
[45] Date of Patent: Nov. 21, 1989

[54] PHARMACEUTICAL FOR TREATING TUMORS AND METHOD FOR MAKING IT

[75] Inventors: Kuslima Shogen, Somerset; Stanislaw M. Mikulski, Essex Fells; Wojciech J. Ardelt, Passaic, all of N.J.

[73] Assignee: Alfacell Corporation, Bloomfield, N.J.

[21] Appl. No.: 178,118

[22] Filed: Apr. 6, 1988

Related U.S. Application Data

[63] Continuation-in-part of Ser. No. 776,798, Sep. 17, 1985, which is a continuation-in-part of Ser. No. 643,808, Aug. 23, 1984, abandoned, which is a continuation of Ser. No. 422,034, Sep. 23, 1982, abandoned.

[51] Int. Cl.$^4$ .......................... C07K 3/02; C07K 3/12
[52] U.S. Cl. ...................................... 530/350; 514/2; 424/105; 530/323; 530/324; 530/412; 530/853; 530/850

[58] Field of Search ............... 530/350, 412, 323, 322, 530/324, 850, 853, 412; 514/2; 424/105

[56] References Cited

U.S. PATENT DOCUMENTS

| | | | |
|---|---|---|---|
| 4,112,074 | 9/1978 | Truffier et al. | 424/105 |
| 4,340,591 | 7/1982 | Lucotte et al. | 424/105 |

*Primary Examiner*—Sam Rosen
*Attorney, Agent, or Firm*—Mark H. Jay

[57] ABSTRACT

*Rana pipiens* eggs are subjected to fertilization and the embryos are grown to a predetermined stage of development. The embryos and unfertilized eggs are then subjected to mechanical processing in the presence of a weakly acidic buffer to produce an extract. The extract is subjected to ion-exchange chromatography and size-exclusion chromatography.

The resulting pharmaceutical has activity against certain cancer cells. A partial amino acid sequence of the pharmaceutical is disclosed.

21 Claims, 3 Drawing Sheets

FIG. 3

Ser-Thr- Asn -Leu-Phe-His-Cys-Lys-Asp-Lys- Asn -Thr-Phe-Ile-Tyr-Ser-
         Asp                              Asp

Arg-Pro-Glu-Pro-Val-Lys-Ala-Ile- (Cys) -Lys-Gly-Ile-Ile-Ala-Ser-

Lys-Asn-Ala-Val-Leu-Thr-Thr-Ser-Glu-Phe-Tyr-Leu-Ser-Asp-Xxx-Asn-

Val-Thr-Xxx- (Lys) -Pro-Xxx-Lys- (Tyr) - (Cys) - (Phe)

( ) = RESIDUE IDENTIFIED WITH A LEVEL OF CONFIDENCE BETWEEN
      80% AND 100%

___ = RESIDUES WHICH MAY BE IN INVERTED ORDER

Xxx = UNIDENTIFIED RESIDUE

Asn
Asp = POLYMORPHISM

PHARMACEUTICAL FOR TREATING TUMORS AND METHOD FOR MAKING IT

CROSS-REFERENCE TO RELATED APPLICATIONS

This application is a continuation-in-part of a pending commonly-owned application filed Sept. 17, 1985, accorded serial number 776,798 and entitled "Pharmaceutical for Treating Tumors in Humans and Method for Making It", which is a continuation-in-part of a pending commonly-owned application filed Aug. 23, 1984, accorded Ser. No. 643,808, and entitled "Non-Specific Tumor Treatment" (now abandoned), which is a continuation application of Ser. No. 422,034, filed Sept. 23, 1982 (now abandoned). The disclosures of all these related applications are hereby incorporated herein by reference as if fully set forth.

BACKGROUND OF THE INVENTION

The invention relates to pharmaceuticals, and more particularly relates to pharmaceuticals for use in treating tumors in humans.

At present, tumors are treated either by chemotherapy, radiotherapy or surgery. Each of these therapies has disadvantages.

It would be advantageous to avoid the disadvantages of chemotherapy, radiotherapy and surgery.

One object of the invention is to provide a pharmaceutical therapy for tumors in humans.

Another object is to provide such a therapy which has less disadvantageous side effects than those of other known therapies.

A further object is to provide such a therapy for use with more than one type of tumor.

Still a further object is, in general, to improve on known therapies for treatment of tumors in humans.

In accordance with the invention, there is provided a pharmaceutical for treatment of tumors in humans. The pharmaceutical is a substantially pure protein having a molecular weight of approximately 14,000–16,000 Daltons and having a characteristic isoelectric point and amino acid composition. Advantageously although not necessarily, the pharmaceutical is derived from frog egges subjected to fertilization, in a preferred embodiment, the pharmaceutical is derived from embryos and eggs of the *Rana pipiens* frog. The development of the embryos is advantageously halted before gastrulation and preferably at or before the full blastulae (128 cell) stage, and the embryos are homogenized in the presence of a weakly acidic buffer and then centrifuged to derive a supernatant liquid. This is then subjected to ion-exchange chromatography and size-exclusion chromatography.

BRIEF DESCRIPTION OF THE DRAWINGS

The invention will be better understood with reference to the following illustrative and non-limiting drawings, in which:

FIG. 3 is an illustration of the sequence of amino acids in the longer fragment of the pharmaceutical after cleavage using cyanogen bromide.

DETAILED DESCRIPTION OF PREFERRED EMBODIMENTS

A. Production of Embryo/Egg Mixture

Figure 1:
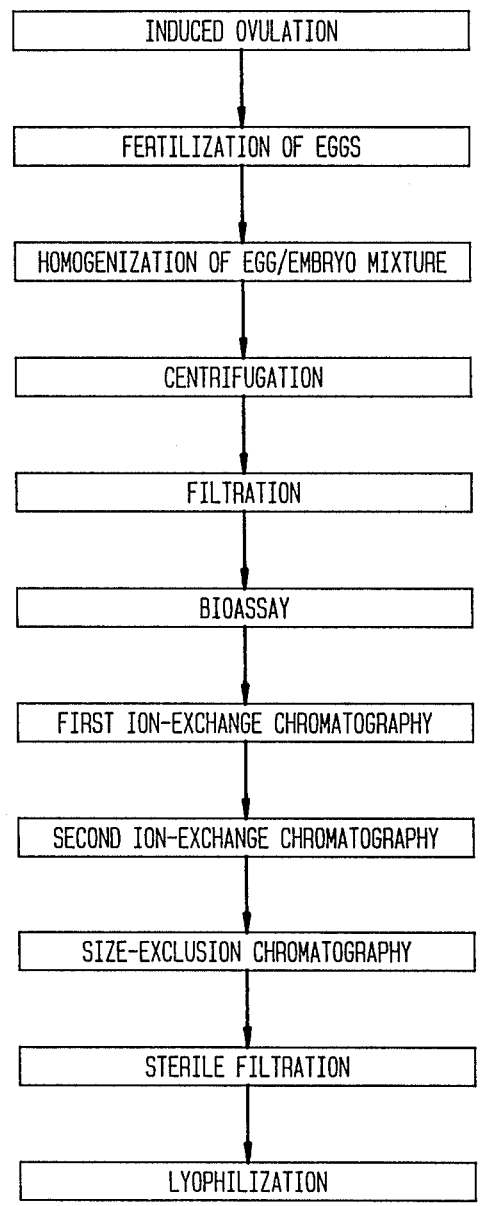
FIG. 1 is a flow chart of the process in accordance with a preferred embodiment of the invention.
Figure 2:
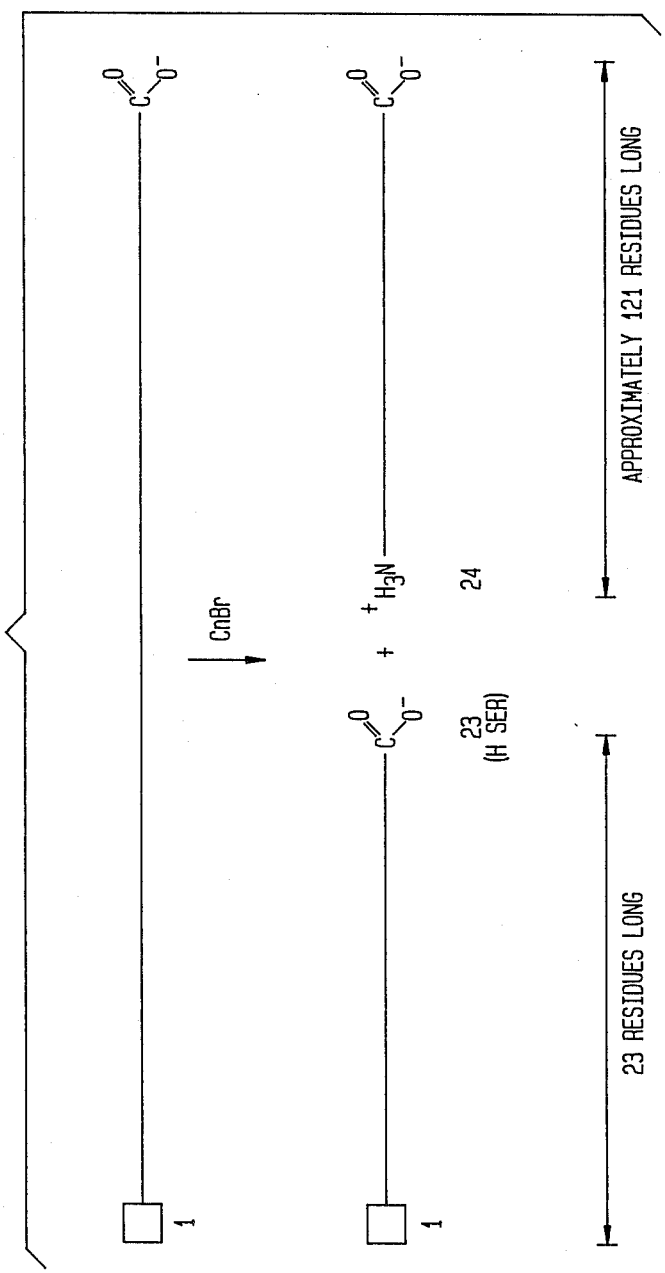
FIG. 2 is a schematic representation of the cleavage of the pharmaceutical using cyanogen bromide.

In the preferred embodiment, rana pipiens eggs are produced by induced ovulation so that their development takes place in a highly controlled manner) and fertilized under controlled conditions outside the body of the female frog. Ovulation is only induced during the months from September through March; during the other months, induced ovulation is not feasible. This is because rana pipiens ovulates spontaneously in the month of and its breeding season lasts from May through August.

Only large, healthy and vigorous gravid female rana pipiens are selected for induced ovulation. They are separated from male rana pipiens and are maintained at a temperature of 6° C. for a period of three days in tanks filled with one inch of tap water. This temperature is preferred, but other temperatures can be used if the other variables in the fertilization process are accordingly adjusted; the rate at which the eggs develop is dependent upon temperature.

For each selected female, a petri dish is preferably filled with 10 cubic centimeters of tested spring water. Tested spring water is fresh spring water which has been tested to support life of rana pipiens and its embryos.

Advantageously, each selected female is induced to ovulate by introducing 5 freshly isolated female rana pipiens pituitary glands into her body. Male pituitary glands may be substituted for female pituitary glands, but one female pituitary gland is equivalent to two male pituitary glands and the quantities used must be adjusted accordingly.

The appropriate number of glands is placed in the corresponding liquid-containing petri dish. Each selected female is brought to room temperature (22° C.). Dish by dish, the glands are drawn up into a syringe and introduced into the right lower quadrant of the abdomen of the corresponding selected female by injection through an 18 gauge needle.

The selected females are then replaced in tanks filled with one inch of spring water. Flat rocks are placed in the bottom of each tank, so that the females can rest upon them and remain above the water line. (This is advantageous because gravid females can become lethargic and may drown if not held above the water line). The tanks are covered with warehouse cloth (to prevent the frogs from jumping out of the tanks) and advantageously kept at room temperature (22° C.) for 48 hours. The eggs produced by the gravid females are then, in accordance with the preferred embodiment, subjected to fertilization outside the bodies of the female frogs, advantageously in petri dishes, and preferably in 4 petri dishes per gravid female.

To accomplish this fertilization, male *Rana pipiens* are sacrificed (as by over-etherization) and their testes are removed and cleaned of connective tissue and fat. Enough males must be killed to yield at least 4 testes per petri dish of eggs to be fertilized (i.e. 16 testes per gravid female). This quantity produces an optimized quantity of sperm suspension considering the size of the petri dishes. (Advantageously, the pituitary glands of the male *Rana pipiens* are also removed for subsequently inducing ovulation in other females).

Four testes are then placed in each petri dish, and the testes are macerated (as by chopping) to form a milky sperm suspension. The maceration must be conducted in such a manner as not to chop the sperm. The eggs are then removed from each gravid female by pressing her abdomen towards her posterior. The egg production of each female is distributed evenly among four suspension-filled petri dishes; this avoids overcrowding the eggs in the dishes.

The eggs are left in the suspension for about 3 to 4.5 hours at room temperature. During the first hour, the sperm suspension and eggs in the dish are intermittently swirled so that the eggs are always covered by the sperm suspension after the 3 to 4.5 hours have passed, the dishes are checked under a dissecting microscope for signs of cleavage. When 80% cleavage of the *Rana pipiens* embryos is observed, the corresponding dish is collected; the embryos are then in at least the 4 cell stage of development. The 4 cell stage of development is used as a benchmark because it establishes division of the eggs and the existing fact of fertilization cannot be overlooked.

Since 100% cleavage of the embryos is not ordinarily achieved in the stated 3 to 4.5 hour time, the collected dishes will ordinarily contain both embryos (fertilized eggs) and unfertilized eggs. This mixture will be occasionally referred to as a mixture of eggs subjected to fertilization, meaning that both eggs and embryos are present. Since 80% cleavage is used as a benchmark in the preferred embodiment, the ratio of eggs to embryos in the mixture is approximately 1:4.

All collected eggs subjected to fertilization may then be scraped into containers and stored in frozen form at $-15°$ C. to $-20°$ C. This storage is not essential for the practice of the invention; it is preferred only when it is convenient to carry out subsequent processing in batches.

B. MECHANICAL PROCESSING OF THE EGGS SUBJECTED TO FERTILIZATION

If the mixture has been frozen, it is thawed by any method which does not overheat it. The thawed or never-frozen mixture is then homogenized in the presence of a weakly acidic buffer, preferably under a laminar air flow hood to avoid contamination.

In the preferred embodiment, the mixture of eggs subjected to fertilization is mixed, at room temperature, with 0.15M sodium acetate (pH 4.8–4.9) using two volumes of buffer for one like volume of the mixture of eggs subjected to fertilization. The buffer need not be sodium acetate but must be weakly acidic; sodium acetate is used because, in the preferred embodiment, (M-sepharose chromatography is carried out and sodium acetate is a good buffer within a pH range of 4–5.8 (in which range CM-sepharose exchange columns are efficient). Homogenization is carried out in a Waring Blender until all eggs have been disrupted as observed visually, but a Waring Blender is not required and any sanitary method for accomplishing thorough homogenization can be used. Homogenization is complete when the suspension appears homogenous with no visual sign of intact eggs. The homogenate is then stirred at room temperature for 2 hours.

In the preferred embodiment, the stirred homogenized mixture of eggs subjected to fertilization is centrifuged (at 4° C. to 8° C.) in two stages. In the first stage, the stirred homogenate is centrifuged at an average acceleration of $350,000 \times g$ and the resulting supernatant is saved. The time required for this step is usually 30 minutes, but it is necessary to obtain clear and gel-free supernatant and the time is increased as necessary to achieve this. In the second stage, the sediment pellet which results from the first stage of centrifugation is re-homogenized as above, but this time using one volume of the buffer for one like volume of the sediment pellet. The re-homogenized sediment is then centrifuged as above, and the resulting supernatant is then pooled with the supernatant produced in the first step.

The duration, speed, and other particulars of the centrifugation steps described above were chosen to apply the maximum g-forces to the homogenate and sediment in the most convenient manner, using the equipment available. They are not required to practice the invention, but they are optimized for the preferred embodiment of the invention.

As each batch of supernatant fluid is decanted, it is filtered through sterile gauze and then, in the preferred embodiment, is clarified by pressure filtration through a Gelman extra-thick glass fiber filter. This is to remove debris which could clog the columns in the processing steps described below, but the use of a Gelman extra-thick glass fiber filter is not required and other suitable filters could be used instead.

In the preferred embodiment, the filtered extract is assayed for bioactivity against a predetermined cell line. This is not required but, for two main reasons, is advantageous. The first reason is that in a process which is scaled to commercial production quantities, batches of filtered extract are pooled together before subsequent processing steps are undertaken. By checking for and discarding batches of inactive filtered extract, inadvertent contamination of bioactive batches with nonbioactive ones is eliminated. The other reason is that the subsequent processing steps are expensive, and identification and rejection of nonbioactive material saves the substantial expensive which would otherwise be wasted on processing it.

The actual assay used in the preferred embodiment is performed using human submaxillary epidermoid carcinoma A-253 cells and a tetrazolium compound sold by Chemicon International, Inc., 100 Lomita Street, El Segundo, Calf., under the MTT trademark. However, this is not necessary and other bioassays may be used. Alternatively, a bioassay may be unnecessary if an alternate non-bioassay method which correlates well with a bioassay is available.

The filtered extract is frozen at $-15°$ C. to $-20°$ C. for storage or immediately subjected to further purification steps. Frozen storage is preferred because it prevents bacterial growth, degradation and denaturation of the proteins in the extract.

C. Ion-Exchange Chromatography

If the filtered extract was frozen, it is thawed by any method which does not overheat it. The thawed or non-frozen extract is then subjected to ion-exchange chromatography. In the preferred embodiment, the ion-exchange chromatography is carried out in two steps under slightly different conditions. During the first step, the active protein is initially isolated and essentially freed of endotoxin. During the second step, the protein is purified from other proteins which have been copurified with the active protein during the first step as well as from any possible persisting endotoxin.

In the preferred embodiment, the first ion-exchange chromatography step is carried out using a column which is 11 cm in diameter and 20 cm long. The conditions described below are optimized for columns of these dimensions. However, if differently-dimensioned columns are used, the conditions may change.

In the preferred embodiment, the purpose of the two consecutive ion-exchange chromatography steps is to isolate proteins with isoelectric points pI of 9.5–10.5 before isolating the proteins by size. In the first ion-exchange chromatography step, the filtered extract is acidified to pH 4.5 with acetic acid and loaded onto a column which is filled with CM-Sepharose gel. The column is equilibrated in a 0.15M sodium acetate buffer (pH 4.5) and the column is developed with a continuous linear gradient of sodium chloride (0–0.7M) made in the equilibrating buffer. These conditions are not necessary to practice the invention but they are convenient and, at present, seem to produce good working yields of bioactive protein.

In the preferred embodiment, the eluted protein is then diluted 2 times with pyrogen-free water and subjected to a second ion-exchange chromatography step which is carried out under different conditions. This second ion-exchange chromatography step is performed on a second column which is 5 cm in diameter and 20 cm long and is filled with CM-Sepharose gel. The column is equilibrated in a 0.15M sodium acetate buffer (pH 4.8) and the column is developed with a continuous linear gradient of sodium chloride (0–0.4M) made in the equilibrating buffer.

Advantageously, both chromatography steps are carried out at 18° C.–20° C. (air conditioned room), but this is not critical. Column chromatography is known to be more efficient above 4° C. (cold-room) temperatures and the process is carried out at the highest temperature which is consistent with stability of the purified pharmaceutical.

In the preferred embodiment, the from the second ionexchange step is concentrated by ultafiltration using a membrane which has a 5000 Daltons molecular weight cutoff and discarding the permeate. Suitable membranes are the Spectra-Por (manufactured by Spectrum Medical Industries) and the Amicon YM5 (manufactured by Amicon), but other membranes and other concentration procedures may be used instead.

D. Size-Exclusion Chromatography

The concentrated material is then loaded onto a column which is 5 cm in diameter and 90 cm long, which is filled with Bio-Gel P-30 gel and which is equilibrated in 0.75 ammonium bicarbonate. The main protein peak is isolated.

These specific conditions are not required to practice the invention; other dimensions, gels and even other size-exclusion techniques could be used instead. However, it is recommended that the size-exclusion chromatography follow the ion-exchange chromatography. This is because this order of chromatography makes it possible to use a column of reasonable size for the size-exclusion chromatography.

E. Final Processing

The eluate from the size-exclusion column is then sterile filtered through a 0.22 micron filter and subsequently lyophilized (freeze-dried). These process steps are standard in the pharmaceutical industry, and are not a part of the invention. The resultant preparation is devoid of viable micro-organisms.

BIOACTIVITY OF THE PHARMACEUTICAL

Confirmatory in vitro andinvivo animal data show that the pharmaceutical is active against human submaxillary epidermoid carcinoma A-253 cells and human ovarian adenocarcinoma NIH-OVCAR-3 cells. This pharmaceutical has also shown activity against human leukemic HL-60 cells, human COLo320 DM cells originally isolated from colon adenocarcinoma, human LOX melanoma, and human lung squamous carcinoma HT-520 cells.

CHEMICAL ANALYSIS AND COMPOSITION OF THE PHARMACEUTICAL

The pharmaceutical described above has been characterized to some extent. While the pharmaceutical is a protein isolated from Rana pipiens, it is believed that the pharmaceutical may be produced using genetic engineering techniques, as long as the end result has the following chemistry and structure:

The pharmaceutical is a substantially pure protein (i.e. substantially homogeneous, as established by standard tests which are used to assay the homogeneity of proteins). By electrophoresis, the molecular weight of the pharmaceutical is not less than approximately 14,000 Daltons, and amino acid analysis indicates that its molecular weight does not substantially exceed 16,000 Daltons. The pharmaceutical has an isoelectric point pI between 9.5 and 10.5. The pharmaceutical has a blocked amino terminal group and is substantially free of carbohydrates (as determined by anthrone and orcinol methods) and other proteins. Amino acid analysis reveals that the pharmaceutical has the following amino acid composition:

| AMINO ACID | APPROX. # OF RESIDUES PER MOLECULE OF MATERIAL |
| --- | --- |
| Aspartic acid/Asparagine | 20 |
| Threonine | 13 |
| Serine | 11 |
| Glutamic acid/Glutamine | 9 |
| Proline | 6 |
| Glycine | 4 |
| Alanine | 4 |
| Cystine/2 | 10 |
| Valine | 11 |
| Methionine | 1 |
| Isoleucine | 8 |
| Leucine | 7 |
| Tyrosine | 3 |
| Phenylalanine | 8 |
| Histidine | 4 |
| Lysine | 17 |
| Arginine | 4 |
| Tryprophan | 2 |
| Approximate Total | 142 |

When the pharmaceutical is cleaved at the methionine residue using cyanogen bromide as described by G. Allen in T. S. Work and R. H. Burdon, eds., *Sequencing of Proteins and Peptides*, (Elsevier/North-Holland, 1981), pp. 43–71, and then reduced and carboxymethylated as described by G. Allen, op. cit., pp. 17–142, two fragments of different lengths are created. These fragments are then separated by size exclusion chromatography. The amino acid compositions of these fragments are as follows:

| SHORTER FRAGMENT | |
| --- | --- |
| AMINO ACID | APPROX. # OF RESIDUES PER MOLECULE OF MATERIAL |
| Aspartic acid/Asparagine | 20 |
| Threonine | 6 |
| Serine | 3 |

SHORTER FRAGMENT

| AMINO ACID | APPROX. # OF RESIDUES PER MOLECULE OF MATERIAL |
|---|---|
| Glutamic acid/Glutamine | 0 |
| Proline | 2 |
| Glycine | 0 |
| Alanine | 0 |
| Cystine/2 | 0 |
| Valine | 1* |
| Methionine | 1 |
| Isoleucine | 1** |
| Leucine | 2 |
| Tyrosine | 1 |
| Phenylalanine | 0 |
| Histidine | 1 |
| Lysine | 1 |
| Arginine | 1 |
| Tryprophan | 1 |
| Approximate Total | 23 |

*(as carboxymethyl-cysteine)
**(as homoserine and homoserine lactone)

LONGER FRAGMENT

| AMINO ACID | APPROX. # OF RESIDUES PER MOLECULE OF MATERIAL |
|---|---|
| Aspartic acid/Asparagine | 15 |
| Threonine | 10 |
| Serine | 10 |
| Glutamic acid/Glutamine | 7 |
| Proline | 6 |
| Glycine | 5 |
| Alanine | 4 |
| Cystine/2 | 9 |
| Valine | 10 |
| Methionine | 0 |
| Isoleucine | 6 |
| Leucine | 6 |
| Tyrosine | 4 |
| Phenylalanine | 7 |
| Histidine | 3 |
| Lysine | 15 |
| Arginine | 3 |
| Tryprophan | 1 |
| Approximate Total | 121 |

The cystine/2 (cysteine) residue appears as carboxymethylcysteine because of reduction and alkylation of the disulphide bridges. The methionine residue appears as a mixture of homoserine and homoserine lactone because of the CNBr cleavage of the chain after methionine.

The shorter fragment has an apparently blocked amino terminal, a homoserine carboxy terminal and a length of approximately 23 residues. (The effect of the blocked or free status of the amino terminal on the activity of the pharmaceutical is undetermined.) The longer fragment has a free amino terminal and a length of approximately 121 residues. The longer fragment contains an amino acid sequence expressed as Ser—Thr—$\frac{Asn}{Asp}$—Leu—Phe—His—Cys—Lys—Asp—Lys—

—$\frac{Asn}{Asp}$—Thr—Phe—Ile—Tyr—Ser—Arg—Pro—Glu—

—Pro—Val—Lys—Ala—Ile—(Cys)—Lys—Gly—Ile—Ile—

—Ala—Ser—Lys—Asn—<u>Ala—Val</u>—Leu—Thr—Thr—Ser—

—Glu—Phe—Tyr—Leu—Ser—Asp—Xxx—Asn—Val—Thr—

—Xxx—(Lys)—Pro—Xxx—Lys—(Tyr)—(Cys)—(Phe)

beginning immediately after the methionine residue. In this expression, residues which have been identified with a level of confidence which is less than 100% but is at least 80% are shown within parentheses. Xxx indicates an unidentified residue, and underlined residues might be inverted order. The $\frac{Asn}{Asp}$ polymorphism may represent allelic polymorphism or a different degree of amidation.

Although a preferred embodiment has been described above, the scope of the invention is limited only by the following claims:

We claim:

1. A substantially pure protein having a molecular weight of approximately 14,000 to 16,000 Daltons and an amino acid composition approximately as follows:

| AMINO ACID | APPROX. # OF RESIDUES PER MOLECULE OF MATERIAL |
|---|---|
| Aspartic acid/Asparagine | 20 |
| Threonine | 13 |
| Serine | 11 |
| Glutamic acid/Glutamine | 9 |
| Proline | 6 |
| Glycine | 4 |
| Alanine | 4 |
| Cystine/2 | 10 |
| Valine | 11 |
| Methionine | 1 |
| Isoleucine | 8 |
| Leucine | 7 |
| Tyrosine | 3 |
| Phenylalanine | 8 |
| Histidine | 4 |
| Lysine | 17 |
| Arginine | 4 |
| Tryprophan | 2 |
| Approximate Total | 142 |

2. A substantially pure protein derived from frog eggs which have been subjected to fertilization, the protein having a molecular weight of approximately 15,000 Daltons, an isoelectric point pI of 9.5 to 10.5 and a blocked amino terminal group, the protein being substantially free of carbohydrates and other proteins.

3. A substantially pure protein which has a single methionine residue and which, when cleaved with cyanogen bromide at said residue, produces a shorter fragment and a longer fragment, the shorter fragment having a blocked amino terminal, a homoserine plus homoserine lactone carboxy terminal and a length of approximately 23 residues, and the longer fragment having a free amino terminal group and a length of approximately 121 residues, and the longer fragment containing an amino acid sequence expressed as Ser—Thr—$\frac{Asn}{Asp}$—Leu—Phe—His—Cys—Lys—Asp—Lys—

—$\frac{Asn}{Asp}$—Thr—Phe—Ile—Tyr—Ser—Arg—Pro—Glu—

—Pro—Val—Lys—Ala—Ile—(Cys)—Lys—Gly—Ile—Ile—

-continued

—Ala—Ser—Lys—Asn—Ala—Val—Leu—Thr—Thr—Ser—

—Glu—Phe—Tyr—Leu—Ser—Asp—Xxx—Asn—Val—Thr—

—Xxx—(Lys)—Pro—Xxx—Lys—(Tyr)—(Cys)—(Phe)

in which sequence amino acid residues which have been identified with a level of confidence which is less than 100% and is at least 80% have been shown within parentheses, in which Xxx indicates an unidentified residue, in which underlined residues might be in inverted order, and in which there is an apparent polymorphism of Asn and Asp where they are listed in a common position.

4. A substantially pure protein which has a single methionine residue and which, when cleaved with cyanogen bromide at said residue, produces a shorter fragment and a longer fragment, the amino acid composition of the fragments being approximately as follows:

| SHORTER FRAGMENT | |
|---|---|
| AMINO ACID | APPROX. # OF RESIDUES PER MOLECULE OF MATERIAL |
| Aspartic acid/Asparagine | 20 |
| Threonine | 6 |
| Serine | 3 |
| Glutamic acid/Glutamine | 0 |
| Proline | 2 |
| Glycine | 0 |
| Alanine | 0 |
| Cystine/2 | 0 |
| Valine | 1* |
| Methionine | 1 |
| Isoleucine | 1** |
| Leucine | 2 |
| Tyrosine | 1 |
| Phenylalanine | 0 |
| Histidine | 1 |
| Lysine | 1 |
| Arginine | 1 |
| Tryprophan | 1 |
| Approximate Total | 23 |

*(as carboxymethyl-cysteine)
**(as homoserine and homoserine lactone)

| LONGER FRAGMENT | |
|---|---|
| AMINO ACID | APPROX. # OF RESIDUES PER MOLECULE OF MATERIAL |
| Aspartic acid/Asparagine | 15 |
| Threonine | 10 |
| Serine | 10 |
| Glutamic acid/Glutamine | 7 |
| Proline | 6 |
| Glycine | 5 |
| Alanine | 4 |
| Cystine/2 | 9 |
| Valine | 10 |
| Methionine | 0 |
| Isoleucine | 6 |
| Leucine | 6 |
| Tyrosine | 4 |
| Phenylalanine | 7 |
| Histidine | 3 |
| Lysine | 15 |
| Arginine | 3 |
| Tryprophan | 1 |
| Approximate Total | 121 |

5. A process for producing a purified pharmaceutical, comprising the following steps:
   (a) subjecting eggs of a frog to fertilization and thereby producing embryos;
   (b) terminating development of the embryos prior to gastrualation;
   (c) mechanically homogenizing the embryos and any unfertilized eggs in the presence of a weakly acidic buffer;
   (d) centrifuging said homogenized embryos and eggs to derive a supernatant liquid therefrom; and
   (e) subjecting the supernatant liquid to ion-exchange chromatography
to thereby obtain a purified pharmaceutical.

6. The process of claim 5, further comprising the step of concentrating material which has been recovered by said ion-exchange chromatography step.

7. The process of claim 6, further comprising the step of subjecting said recovered and concentrated material to size-exclusion chromatography.

8. The process of claim 5, wherein the frog is Rana pipiens.

9. The process of claim 5, wherein the buffer is sodium acetate.

10. The process of claim 5, wherein the ion-exchange chromatography is of the cation exchange type.

11. The process of claim 5, further comprising the step of filtering the supernatant liquid prior to subjecting the supernatant to ion-exchange chromatography.

12. The process of claim 11, wherein said filtering step is carried out by filtering the supernatant liquid through a Gelman extra-thick glass fiber filter.

13. A process for producing a pharmaceutical, comprising the following steps:
   (a) subjecting eggs of a frog to fertilization and thereby producing embryos;
   (b) terminating development of the embryos prior to gastrulation;
   (c) mechanically homogenizing the embryos and any unfertilized eggs in the presence of a weakly acidic buffer;
   (d) centrifuging said homogenized embryos and eggs to derive a supernatant liquid therefrom; and
   (e) extracting, from the supernatant liquid, materials having an isoelectric point between 9.5 and 10.5.

14. The process of claim 13, wherein said extracting step comprises the step of ion-exchange chromatography.

15. The process of claim 13, further comprising the step of isolating from said materials those with molecular weights between approximately 14,000 Daltons and 16,000 Daltons.

16. The process of claim 15, wherein said isolating step comprises the step of size-exclusion chromatography.

17. A process for producing a pharmaceutical, comprising the following steps performed in the order listed:
   (a) subjecting eggs of a frog to fertilization and thereby producing embryos;
   (b) terminating development of the embryos prior to gastrulation;
   (c) mechanically homogenizing the embryos and any unfertilized eggs in the presence of a weakly acidic buffer;
   (d) centrifuging said homogenized embryos and eggs to derive a supernatant liquid therefrom;

(e) subjecting the supernatant liquid to ion-exchange chromatography and thereby recovering a material;
(f) subjecting said material to a second step of ionexchange chromatography under different conditions and thereby recovering a purer material; and
(g) subjecting said purer material to size-exclusion chromatography.

18. The process of claim 17, wherein
the first of said two ion-exchange chromatography steps is carried out using a CM-Sepharose gel which is equilibrated in a sodium acetate buffer and developed using a first continuous linear sodium chloride gradient,
and wherein
the second of said two ion-exchange chromatography steps is carried out using the same CM-Sepharose gel which is equilibrated in a sodium chloride buffer and developed using a second continuous linear sodium chloride gradient which is different from said first continuous linear sodium chloride gradient.

19. The process of claim 17, wherein said size-exclusion chromatography step is carried out using a column which is filled with Bio-Gel P-30 gel and is equilibrated in ammonium bicarbonate.

20. A process for manufacturing a pharmaceutical, comprising the following steps performed in the order listed:
(a) creating embryos of the *Rana pipiens* frog by fertilization of *Rana pipiens* eggs with *Rana pipiens* sperm outside the body of a female *Rana pipiens;*
(b) terminating development of the embryos at approximately the 4 cell stage;
(c) mechanically homogenizing the embryos and any unfertilized eggs in a weakly acidic buffer;
(d) centrifuging said homogenized embryos and eggs to derive a supernatant liquid therefrom;
(e) filtering the supernatant liquid;
(f) subjecting the filtered supernatant liquid to ion-exchange chromatography and thereby recovering a material;
(g) re-subjecting said recovered material to a second step of ion-exchange chromatography under slightly different conditions and thereby recovering a purer material; and
(h) subjecting said purer material to size-exclusion chromatography and thereby recovering a purified material.

21. The process of claim 20, further comprising the step of lyophilizing said purified material.

* * * * *

Disclaimer 4,882,421.—*Kuslima Shogen*, Somerset; *Stanislaw M. Mikulski*, Essex Fells; *Wojciech J. Ardelt*, Passiac, all of N.J. PHARMACEUTICAL FOR TREATING TUMORS AND METHOD FOR MAKING IT. Patent dated Nov. 21, 1989. Disclaimer filed July 27, 1990, by the assignee, Alfacell Corp.

Hereby enters this disclaimer to claims 1, 3 and 4 of said patent.
[ *Official Gazette December 18, 1990* ]

UNITED STATES PATENT AND TRADEMARK OFFICE
CERTIFICATE OF CORRECTION

PATENT NO. : 4,882,421

DATED : November 21, 1989

INVENTOR(S) : Kuslima Shogen, Stanislaw M. Mikulski and Wojciech J. Ardelt

It is certified that error appears in the above-identified patent and that said Letters Patent is hereby corrected as shown below:

Column 1, line 46: change "egges" to --eggs--; change "," to --;--

Column 2, line 6: change "so" to --(so--

Column 2, line 13: between "of" and "and", insert --April--

Column 2, line 49: change "line)." to --line.)--

Column 5, line 66: change "in vitro andinvivo" to --*in vitro* and *in vivo*--

Column 6, line 4: change "COLo320" to --COLO 320--

UNITED STATES PATENT AND TRADEMARK OFFICE
CERTIFICATE OF CORRECTION

PATENT NO. : 4,882,421

DATED : November 21, 1989

INVENTOR(S) : Kuslima Shogen, et al

It is certified that error appears in the above-identified patent and that said Letters Patent is hereby corrected as shown below:

Column 11, claim 17, subparagraph (f): change "ionexchange" to

--ion-exchange--.

Signed and Sealed this

Eighteenth Day of June, 1991

*Attest:*

HARRY F. MANBECK, JR.

*Attesting Officer*       *Commissioner of Patents and Trademarks*